(12) United States Patent
Chroust et al.

(10) Patent No.: US 11,795,140 B2
(45) Date of Patent: Oct. 24, 2023

(54) UREA PRODUCTION WITH TRIPLE MP STREAMS

(71) Applicant: STAMICARBON B.V., Sittard (NL)

(72) Inventors: Josef Chroust, Maastricht (NL); Wilhelmus Hubertus Geurts, Born (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 18/006,046

(22) PCT Filed: Jun. 10, 2022

(86) PCT No.: PCT/NL2022/050325
§ 371 (c)(1),
(2) Date: Jan. 19, 2023

(87) PCT Pub. No.: WO2022/260524
PCT Pub. Date: Dec. 15, 2022

(65) Prior Publication Data
US 2023/0227402 A1    Jul. 20, 2023

(30) Foreign Application Priority Data
Jun. 11, 2021 (EP) ................... 21178994

(51) Int. Cl.
*C07C 273/04* (2006.01)
*B01J 19/00* (2006.01)
(Continued)

(52) U.S. Cl.
CPC .......... *C07C 273/04* (2013.01); *B01D 5/0003* (2013.01); *B01D 5/0057* (2013.01);
(Continued)

(58) Field of Classification Search
CPC . B01D 3/00; B01D 3/009; B01D 5/00; B01D 5/0003; B01D 5/0033;
(Continued)

(56) References Cited

U.S. PATENT DOCUMENTS 4,539,077 A * 9/1985 Jonckers ............... C07C 273/04
203/91
6,730,811 B1  5/2004 Mennen
(Continued)

FOREIGN PATENT DOCUMENTS

EP  2844641 A1  3/2015
EP  3233792 A1  10/2017
(Continued)

OTHER PUBLICATIONS

Meessen, Ullmann's Encyclopaedia, chapter Urea, 2010. 39 pages.
(Continued)

*Primary Examiner* — Natasha E Young
(74) *Attorney, Agent, or Firm* — Leason Ellis LLP

(57) ABSTRACT

The disclosure pertains to a urea production plant and process using a high-pressure $CO_2$ stripper, downstream medium-pressure treatment unit and a medium-pressure dissociator receiving urea synthesis solution from the reactor, wherein gas from the treatment unit and dissociator are
(Continued)

condensed in a first condenser and off-gas from the synthesis section is condensed separately in a second condenser. A revamping method is also described.

20 Claims, 1 Drawing Sheet

(51) Int. Cl.
  *B01D 3/00* (2006.01)
  *B01D 5/00* (2006.01)
  *B01D 19/00* (2006.01)
(52) U.S. Cl.
  CPC ........ *B01D 19/0036* (2013.01); *B01J 19/002* (2013.01); *B01J 2219/00024* (2013.01); *B01J 2219/00245* (2013.01)
(58) Field of Classification Search
  CPC .... B01D 5/0039; B01D 5/0057; B01D 19/00; B01D 19/0036; B01J 19/00; B01J 19/0006; B01J 19/002; B01J 2219/00; B01J 2219/00002; B01J 2219/00018; B01J 2219/00024; B01J 2219/00049; B01J 2219/00245; C07C 273/00; C07C 273/02; C07C 273/04
  See application file for complete search history.

(56) References Cited

U.S. PATENT DOCUMENTS

| | | | |
|---|---|---|---|
| 7,982,068 | B2 * | 7/2011 | Zardi .................... C07C 273/04 564/72 |
| 2008/0118414 | A1 | 5/2008 | Pagani et al. |
| 2008/0300422 | A1 | 12/2008 | Mennen |
| 2011/0160486 | A1 | 6/2011 | Gevers et al. |
| 2015/0119603 | A1 | 4/2015 | Van Den Tillaart et al. |
| 2016/0318883 | A1 | 11/2016 | Mennen |
| 2019/0015811 | A1 | 1/2019 | Coloma Gonzalez et al. |
| 2019/0185422 | A1 | 6/2019 | Pustjens et al. |
| 2020/0385339 | A1 | 12/2020 | Patil et al. |

FOREIGN PATENT DOCUMENTS

| | | |
|---|---|---|
| EP | 3707121 A1 | 9/2020 |
| WO | 2009121843 A1 | 10/2009 |
| WO | 2014154454 A1 | 10/2014 |
| WO | 2020130817 A1 | 6/2020 |
| WO | 2021261999 A1 | 12/2021 |

OTHER PUBLICATIONS

World Fertilizer, Sep. 2020 issue, p. 30. 1 page.
Evolve Technologies Brochure, Stamicarbon B.V. 2018. 20 pages.
International Search Report for corresponding International Application No. PCT/NL2022/050325, dated Aug. 19, 2022.

* cited by examiner

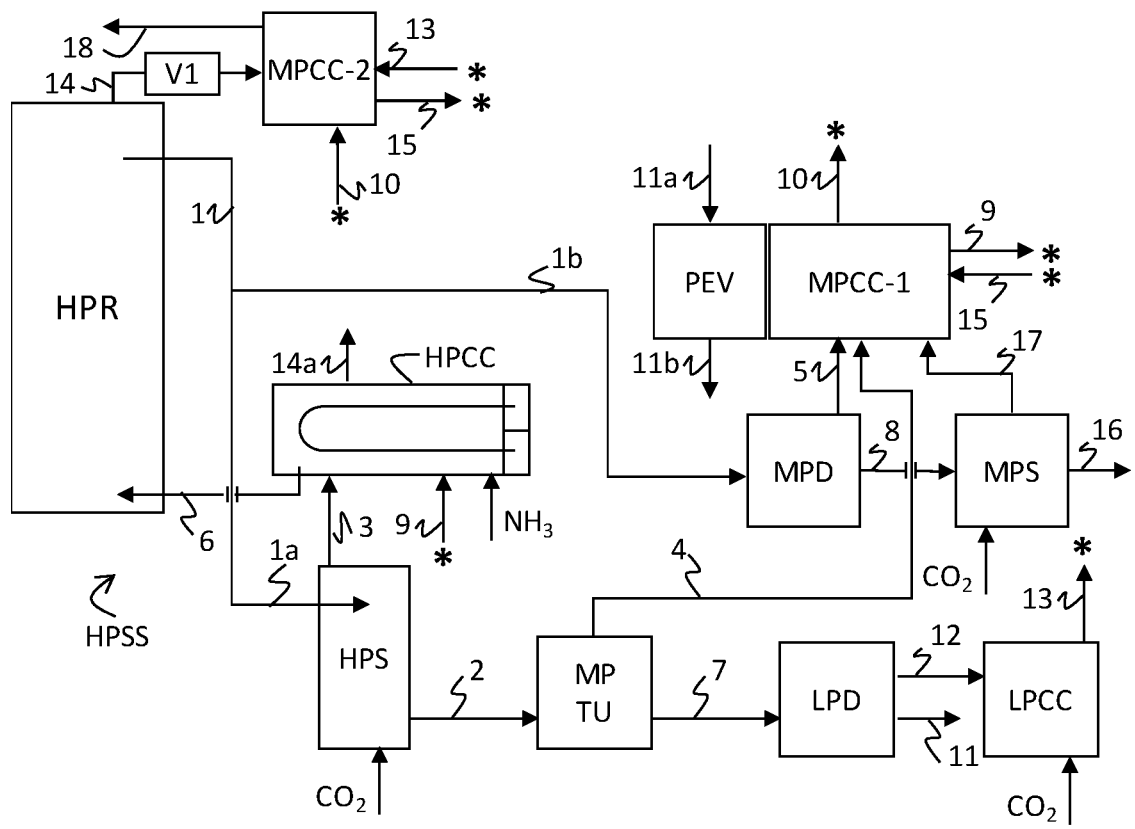

UREA PRODUCTION WITH TRIPLE MP STREAMS

CROSS-REFERENCE TO RELATED PATENT APPLICATIONS

This application is a U.S. National Stage Application under 35 U.S.C. § 371 of International Patent Application No. PCT/NL2022/050325 filed Jun. 10, 2022, which claims the benefit of priority of European Patent Application No. 21178994.6 filed Jun. 11, 2021, both of which are incorporated by reference in their entireties. The International Application was published on Dec. 15, 2022, as International Publication No. WO 2022/260524 A1.

FIELD

The invention pertains to the production of urea from $NH_3$ and $CO_2$.

INTRODUCTION

Urea plants are often of the type with a high pressure (HP) stripper using at least part of the $CO_2$ feed as strip gas (e.g. the Stamicarbon $CO_2$ stripping process). An example process scheme of a urea process of the $CO_2$-stripping type, which does not limit the invention, is shown in Ullmann's Encyclopedia, chapter Urea, 2010, FIG. 16. In the illustrated process, the reactor has an outlet for liquid and an outlet for gas, and the gas from the reactor is supplied to a high-pressure scrubber. Urea solution from the stripper is supplied to a low pressure decomposer and then to a pre-evaporator which is a heat exchanger using cooling water. Gas from the reactor is supplied to the high pressure scrubber. Gas from the low-pressure decomposer or dissociator is condensed in a low pressure carbamate condenser and the resulting carbamate stream containing water is recycled to the synthesis section. Generally low water recycle is desired as supplying water to the reaction zone is detrimental to urea yield. The high pressure stripper in a typical $CO_2$-stripping type urea process is commonly operated with a stripping efficiency alfa of 0.87.

There is a desire for urea production plants and processes with a relatively small HP stripper compared to urea capacity and with low energy consumption. There is also a desire to modify existing urea production plants to increase their capacity.

SUMMARY

The invention pertains in a first aspect to a urea production plant comprising a high pressure (HP) synthesis section comprising an HP stripper, a reaction zone for forming urea from $NH_3$ and $CO_2$, and a condensation zone, wherein the HP stripper has an inlet for $CO_2$ feed as strip gas, the plant further comprising a medium pressure (MP) treatment unit, an MP dissociator, a first MP carbamate condensation section, and a second MP carbamate condensation section, a first flow line for urea solution from said reaction zone to said HP stripper and a second flow line for urea solution from said reaction zone to said MP dissociator, wherein the plant comprises a liquid flow line for stripped urea solution from said HP stripper to said MP treatment unit, wherein the MP treatment unit has a gas outlet for a first MP gas stream, wherein the MP dissociator has a gas outlet for a second MP gas stream, and wherein the HP synthesis section has a gas outlet and a pressure reducing element for a third MP gas stream, and wherein two gas streams selected from the group consisting of said first, second and third MP gas stream are combined and condensed in said first MP carbamate condensation section.

Preferably, said first MP carbamate condensation section is arranged to receive said first MP gas stream from said MP treatment unit and said second MP gas stream from said MP dissociator, and wherein said second MP carbamate condensation section receives said third MP gas stream, preferably wherein said second MP carbamate condensation section comprises a condenser, scrubber and/or absorber.

The invention also pertains to a urea production process carried out in such a urea production plant with such an MP treatment unit, MP dissociator, and first and second MP carbamate condensation section.

The invention also pertains to a method of modifying an existing urea production plant, the existing urea production plant comprising a high pressure (HP) synthesis section comprising an HP stripper, a reaction zone for forming urea from $NH_3$ and $CO_2$, and a condensation zone, wherein the HP stripper has an inlet for $CO_2$ feed as strip gas and the HP synthesis section has a gas outlet, the plant comprising a first flow line for urea solution from said reaction zone to said HP stripper, the method comprising adding, if not already present in the plant, the following units and connections: a medium pressure (MP) treatment unit having a gas outlet for a first MP gas stream, an MP dissociator having a gas outlet for a second MP gas stream, a first MP carbamate condensation section and a second MP carbamate condensation section, and a second flow line for urea solution from said reaction zone to said MP dissociator, a pressure reducing element for gas from said gas outlet of said HP synthesis section giving a third MP gas stream, a liquid flow line for stripped urea solution from said HP stripper to said MP treatment unit, the method further comprising configuring the plant such that two gas streams selected from the group consisting of said first, second and third MP gas stream are combined and condensed in a first MP carbamate condensation section and one gas stream selected from said group is condensed separately in a second MP carbamate condensation section, preferably by arranging the first MP carbamate condensation section to receive said first MP gas stream from said MP treatment unit and said second MP gas stream from said MP dissociator and arranging the second MP carbamate condensation section to receive said third MP gas stream.

BRIEF DESCRIPTION OF THE DRAWINGS

FIG. 1 schematically illustrates an example urea production plant and process according to the invention.

The embodiment illustrated in the figure is an example only and does not limit the invention.

DETAILED DESCRIPTION

The present invention is in an aspect based on the judicious insight of combining MP treatment, in particular adiabatic flash, of stripped urea solution from the HP stripper in an MP treatment unit, to give a first MP gas stream, with MP dissociation of a part of the urea synthesis solution which bypasses the HP stripper in an MP dissociator to give a second gas stream, and reducing the pressure of synthesis section off-gas to MP to give a third MP gas stream. Furthermore, the process involves combining and condensing two of these MP gas streams at medium pressure to form an MP carbamate solution. The MP carbamate solution which is recycled to the HP synthesis section advantageously has low water content thereby improving urea yield in the reaction zone and the heat released in the combined MP condensation can be used advantageously for heat integration.

In an embodiment, the second MP gas stream from the MP dissociator and reactor off-gas as third gas stream are subjected to combined condensation at medium pressure with separate condensation of the first gas stream from the MP treatment unit (e.g. flash vessel).

In an embodiment, the first MP gas stream from the MP treatment unit (e.g. flash vessel) and reactor off-gas as third gas stream are subjected to combined condensation at MP with separate condensation of the second MP gas stream from the MP dissociator.

In a preferred embodiment, the first MP gas stream from the MP treatment unit (e.g. flash vessel) and the second MP gas stream from the MP dissociator are combined and condensed in the first MP carbamate condensation section, giving an advantageous balancing of the N/C ratio, and separate condensation of the reactor off-gas as third MP gas stream. In this embodiment advantageously use is made of the low N/C ratio and low inerts content of the first MP gas stream for condensation of the second MP gas stream from the MP dissociator by combining and condensing said gas streams. Thereby relatively high temperature (by virtue of relatively low inert content) and low water content of the formed MP carbamate solution (by virtue of the N/C ratio) are achieved at a given MP condensation pressure. The high temperature is for instance used for heating urea product solution through heat exchange so as to contribute to water evaporation from the urea solution.

The MP treatment unit is preferably a flash vessel, in particular an adiabatic flash vessel. Adiabatic flashing provides for low $NH_3$ to $CO_2$ molar ratio of the flash vapor (e.g. N/C lower than 1.0). Vapor from the MP adiabatic flashing of stripped urea solution from an HP $CO_2$ stripper comprises e.g. about 40 mol % $NH_3$ and about 50 mol % $CO_2$. The urea solution at the outlet of the flash vessel has a lower temperature than the urea solution at the inlet of the flash vessel in the preferred adiabatic flash.

The off-gas from the synthesis section is for instance released from an HP urea synthesis reactor comprised in the urea production plant. The off-gas for instance contains about 65 mol % $NH_3$ and 20 mol % $CO_2$.

The synthesis section comprises an HP $CO_2$ stripper having an outlet for stripped urea solution connected to an inlet of the MP treatment unit. The HP reaction zone is operated in an example embodiment with an N/C ratio of at least 2.7, for instance about 3, and a pressure of for instance at least 120 bar, e.g. about 140 bar. The urea synthesis solution received in part by the MP dissociator without being subjected to HP $CO_2$ stripping, has a relatively high N/C ratio compared to urea solution at the outlet of the HP $CO_2$ stripper. The urea synthesis solution comprises urea, water, ammonium carbamate, and ammonia. The second gas stream from the MP dissociator also has a relatively high N/C ratio. The second gas stream contains e.g. 65 mol % $NH_2$ and 25 mol % $CO_2$.

The urea production plant and process of the invention are of the $CO_2$ stripping type. The plant comprises a high pressure (HP) synthesis section which comprises an HP stripper, a reaction zone for forming urea from $NH_3$ and $CO_2$, and a condensation zone. The reaction zone comprises one or more reactors. Multiple reactors may be arranged in series or in parallel. The plant comprises for instance a vertical urea reactor. The reaction zone and condensation zone may also be combined in a single vessel, e.g. in a horizontal vessel, such as in a pool reactor. The reaction zone typically has an outlet for urea synthesis solution and a separate outlet for off-gas. The synthesis section has an outlet for off-gas, an outlet for stripped urea solution, and an outlet for non-stripped urea synthesis solution.

The condensation zone is for instance provided by a high pressure carbamate condenser, preferably a shell-and-tube heat exchanger with a tube bundle and a shell side space. For instance a straight tube bundle or U-shaped tube bundle is used. Gas to be condensed is supplied preferably to the shell side space and cooling fluid to the tubes. Alternatively, gas to be condensed is supplied to the tubes and cooling fluid to the shell side space.

The condenser may be a horizontal or a vertical condenser. The condenser is for instance a heat exchanger with a cooling fluid side and a condensation side, configured for operating with liquid as continuous phase on the condensation side, whereas the gases to be condensed are present as bubbles, rising through the liquid phase. This advantageously provides for (substantially) complete condensation in the condenser.

The condenser is for instance a horizontal submerged condenser with cooling fluid in the tubes of for example a U-shaped tube bundle and is for instance a pool condenser or pool reactor, or for instance a vertical condenser with cooling fluid in the tubes, or for instance a vertical condenser with gas to be condensed in the tubes rising up as bubbles in a liquid phase. In still other embodiments, the condenser is for instance a vertical falling film condenser.

The stripper is a heat exchanger having an inlet for $CO_2$ feed used as strip gas and is configured for counter-current contact between a part of the urea synthesis solution from the reaction zone and the strip gas and for heating the urea solution. The $CO_2$ stripper is for instance a vertical shell-and-tube heat exchanger configured for operation with a falling film of urea solution to be stripped in the tubes, and comprising a urea solution inlet at the top, an outlet for stripped urea solution at the bottom, an inlet for strip gas at the bottom and an outlet for gas at the top connected to the HP condensation section, all said inlets and outlets to and from the tubes. The stripper for instance also comprises a shell for a heating fluid such as, for example, steam. In embodiments wherein a separate HP condenser and reactor are used, the plant comprises a flow line for condensate from the condenser to the reactor. The HP carbamate condenser typically also receives the $NH_3$ feed.

The plant comprises a medium pressure (MP) treatment unit, preferably a flash vessel, and a liquid flow line for stripped urea solution from the HP stripper to that MP treatment unit. The MP treatment unit has a gas outlet for a first MP gas stream, and a liquid outlet for a treated urea solution. The plant further comprises an MP dissociator, a first flow line for urea solution from said reaction zone to said HP stripper and a second flow line for urea solution from said reaction zone to said MP dissociator. Hence a part of the urea synthesis solution from the reaction zone, in particular from the reactor, is supplied to the HP stripper and another part to the MP dissociator. In a preferred embodiment, a single reactor is connected to supply urea solution to both the HP stripper and the MP dissociator.

The preferred MP flash vessel is generally operated at a pressure of 10-70 bar, preferably 10-35 bar, for instance 18-25 bar. The preferred MP flash vessel is preferably operated at the same or higher pressure as the MP dissociator, for example at a pressure 0-10 bar higher than the pressure of the MP dissociator, e.g. 1-10 bar higher, or more preferably 2-7 bar higher. The MP dissociator has a gas outlet for a second MP gas stream. The HP synthesis section has a gas outlet for off-gas and a pressure reducing element for that off-gas giving a third MP gas stream. The pressure reducing element is for instance a valve, e.g. a control valve. In the process and plant, two gas streams selected from the group consisting of said first, second and third MP gas stream are combined and condensed in said first MP carbamate condensation section. One gas stream selected from said group is condensed separately in the second MP carbamate condensation section.

The plant preferably comprises gas flow lines for transporting two gas streams selected from the group consisting of said first, second and third MP gas stream to the first MP carbamate condensation section. Preferably, the plant comprises gas flow lines for transporting the first and second MP gas stream to the first MP carbamate condensation section and a gas flow line for supplying the third MP gas stream to the second MP carbamate condensation section.

Preferably, the first MP carbamate condensation section is arranged to receive the first MP gas stream from the MP treatment unit and the second MP gas stream from the MP dissociator. Preferably, the plant comprises a gas flow line from the MP treatment unit to the first MP carbamate condensation section and a gas flow line from the MP dissociator to the first MP carbamate condensation section. Preferably, the plant comprises a gas flow line from said pressure reducing element (or unit) to the second MP carbamate condensation section for supplying the third MP gas stream. In an interesting embodiment, the third MP gas stream from the HP synthesis section has an $NH_3$ content at the inlet of the second MP carbamate condensation section that is at least 90% of the $NH_3$ content (e.g. on mass basis) of the gas stream at the gas outlet(s) of the HP synthesis section. For instance, the gas flow line for the third gas stream from the HP synthesis section to the second MP carbamate condensation section does not include a scrubber or condenser operating at HP.

Preferably, the second MP carbamate condensation section comprises a condenser, scrubber, and/or absorber. Preferably, the second MP condensation section comprises a shell-and-tube heat exchanger (condenser) with cooling fluid, e.g. cooling water, in the tubes and gas to be condensed supplied to the shell side space. Preferably, the heat exchanger also receives a carbamate-containing liquid in the shell side space, for instance in co-current contact with the gas to be condensed. The carbamate-containing liquid is for instance supplied from a low-pressure (LP) recovery section. For instance, gas and liquid are both supplied to a bottom part of the shell side space and the heat exchanger has one outlet at the top. The heat exchanger comprises for instance a U-shaped vertical tube bundle. The condensation section preferably further comprises a gas/liquid separator receiving process fluid from the heat exchanger.

Preferably, the second MP condensation section comprises a shell-and-tube heat exchanger, and a downstream gas/liquid separator, and optionally an absorber receiving gas from said separator.

Preferably, liquid from the absorber is supplied to said heat exchanger, and LP carbamate solution is supplied to the absorber as absorption liquid.

Also in embodiments wherein the second MP condensation section consists of the heat exchanger (as condenser) and gas/liquid separator, i.e. without absorber, the section may be referred to as a scrubber, by analogy to the HP scrubber, frequently used for cleaning off-gas from HP synthesis sections in urea plants of the $CO_2$ stripping type.

In embodiments of the plant and the process according to the invention, the MP treatment unit which is preferably an adiabatic flash vessel makes available a relatively $CO_2$-rich MP gas stream (molar ratio $NH_3$ to $CO_2$ of e.g. less than 1.0, e.g. in the range of 0.80-0.90) and advantageously contributes to lower energy (steam) consumption of the HP stripper. The MP dissociator receiving urea synthesis solution bypassing the HP stripper advantageously allows for relatively large urea production capacity with a relatively small HP stripper. The gas stream from the MP dissociator is relatively $NH_3$-rich (molar ratio $NH_3$ to $CO_2$ of e.g. at least 2.3, e.g. in the range of 2.50-3.0, e.g. about 2.60). This gas steam is preferably combined with the gas stream from the MP treatment unit (preferably the adiabatic flash vessel) and is condensed in the first MP carbamate condensation section at medium pressure (e.g. 20-30 bar, such as 22-30 bar). Such a pressure with low amount of inerts advantageously results in a relatively high temperature of more than 120° C. Preferably, the condensation is carried out in heat exchanging contact with urea solution to be heated for water evaporation. The N/C ratio of the carbamate solution in the first MP carbamate condensation section may be corrected (decreased) by adding a part of the $CO_2$ feed at MP to said first MP carbamate condensation section.

$CO_2$ feed typically contains some inerts and possibly includes oxygen added e.g. for use in a hydrogen convertor. $CO_2$ feed supplied to the first MP carbamate condensation section may for instance be provided from an interstage point of the HP $CO_2$ compressor, or from a dedicated MP $CO_2$ compressor. For example, the supply line for $CO_2$ to the first MP carbamate condensation section comprises a hydrogen converter, typically a catalytic converter, where $H_2$ present as contamination in the $CO_2$ feed is removed. The $CO_2$ feed at the outlet of the hydrogen converter contains for instance 0.05-0.20 vol. % $O_2$, preferably about 0.10 vol. % $O_2$. Advantageously, the $CO_2$ feed stream received by the MP stripper preferably has a lower $O_2$ content than the $CO_2$ feed received by the HP stripper as no or less passivation air is necessary for the units operating at medium pressure.

The $CO_2$ feed may for instance originate from a synthesis gas production section for an upstream ammonia plant.

The $CO_2$ feed is for instance supplied to the first MP carbamate condensation section through an MP stripper which is preferably an adiabatic stripper. The MP stripper is for instance configured for counter-current contacting of urea solution and the $CO_2$ feed and has a gas inlet, gas outlet, liquid inlet and liquid outlet. The MP stripper comprises for instance a packed bed for ensuring gas/liquid contact. Gas from the gas outlet of the MP stripper is supplied to the first MP condensation section. The contacting results in a decrease of the amount of ammonia (free and/or as carbamate) in the urea solution thereby providing for stripping. The urea solution may take up some of the $CO_2$. The $CO_2$ feed stream supplied to the optional MP stripper comprises e.g. at least 95 vol. % $CO_2$ and less than 0.10 vol. % $NH_3$, preferably no $NH_3$. Providing the $CO_2$ feed through an MP stripper is advantageous for instance if the urea solution from the MP dissociator is supplied to an LP recovery section comprising an LP dissociator and an LP carbamate condenser for achieving good carbamate condensation.

Urea solution from the MP treatment unit and urea solution from the MP dissociator is supplied directly or indirectly to an LP recovery section comprising an LP dissociator receiving urea solution and an LP carbamate condenser receiving gas from the LP dissociator. Urea solution from the MP treatment unit and urea solution from the MP dissociator may be processed in a common LP recovery section or in separate LP recovery sections. The LP carbamate condenser(s) also receives water to prevent crystallization of carbamate. The water is for instance provided as clean process condensate, for instance from a waste water treatment section. A part of the $CO_2$ feed is optionally supplied to the LP carbamate condenser, optionally through an atmospheric flash tank condenser, to decrease the N/C ratio of the carbamate solution in the LP carbamate condenser to ensure good condensation and avoid high $NH_3$ supply to an (atmospheric) absorber. Carbamate solution from the LP condensation section is compressed and recycled for instance to the second MP carbamate condenser and comprises for instance 25-50 wt. % $H_2O$, e.g. about 30 wt. % $H_2O$.

Preferably the plant comprises an LP dissociator and a liquid flow line for urea solution from the MP treatment unit to an LP dissociator. Preferably the plant comprises an LP carbamate condenser and a gas flow line from the LP dissociator to the LP carbamate condenser. Preferably, the plant comprises a liquid flow line for carbamate solution from the LP carbamate condenser to the second MP carbamate condensation section (e.g. MP scrubber). Preferably, the plant comprises a liquid flow line for carbamate solution from the second MP carbamate condensation section to the first MP carbamate condensation section. Preferably, the plant comprises a liquid flow line for carbamate solution from said first MP carbamate condensation section to said high pressure (HP) synthesis section, in particular to supply carbamate solution to the reaction zone optionally through the HP condensation zone.

The high pressure synthesis section of the urea plant and process comprises an HP stripper using at least a part of the $CO_2$ feed as strip gas.

The $CO_2$ feed comprises inert components, e.g. from an upstream synthesis gas plant yielding the $CO_2$ feed. Typically the $CO_2$ feed to the HP synthesis section includes oxygen, for instance added for preventing corrosion in the urea synthesis section. Oxygen may also be added for $H_2$ removal in the $CO_2$ feed upstream of the synthesis section. The HP synthesis section comprises one or more outlets for off-gas. The off-gas includes the inert components as well as uncondensed $NH_3$ and $CO_2$. The off-gas from the synthesis section is relatively rich in $NH_3$ (N/C ratio of, e.g., at least 2.2, or in the range 2.3 to 3.0) and is expanded to a pressure in the MP range and is subjected to condensation in the second MP carbamate condensation section.

The condensation is carried out e.g. in the presence of a carbamate recycle stream comprising water from the LP recovery section(s) in a heat exchanger comprised in the second MP carbamate condensation section. Preferably, the plant, in particular the HP synthesis section, does not comprise an HP scrubber. Preferably, the process does not involve contacting the synthesis section off-gas with an aqueous liquid stream at high pressure.

Condensation of the off-gas from the HP synthesis section at medium pressure provides advantages of improved safety and lower equipment costs compared to the use of an HP scrubber.

The second MP carbamate condensation section (e.g. MP scrubber) is for instance operated with cooling water and the temperature at the carbamate outlet is e.g. in the range 80-100° C. The second MP carbamate condensation section is e.g. operated at a pressure of 15-25 bar, preferably 20-25 bar. The carbamate solution from the second MP carbamate condensation section, having e.g. a water content of 25-30 wt. %, is enriched in carbamate in the first MP carbamate condensation section. The first MP carbamate condensation section for instance gives carbamate solution with a water content of e.g. at least 5 wt. % (percent point) lower than the carbamate solution from the second MP carbamate condensation section. The carbamate solution from the first MP carbamate condensation section for instance has a water content in the range 15-20 wt. %. The first MP carbamate condensation section is e.g. operated at a temperature at least 10° C. higher than the second MP carbamate condensation section, e.g. at 110° C.-120° C. In this way the carbamate solution in the second MP carbamate condensation section may have relatively high water content thereby allowing for a lower condensation temperature without a risk of carbamate crystallization. The lower temperature contributes to less venting of non-condensed $NH_3$ to a downstream (LP) absorber. This may contribute to lower energy consumption in a waste water treatment (WWT) section and advantageously smaller recycle from the WWT. The first MP carbamate condensation section is e.g. operated with a pressure of 20-30 bar, preferably 22-27 bar, and preferably with a higher pressure than the second MP carbamate condensation section. Aqueous liquid from the LP absorber may be supplied to the WWT.

Advantageously, inerts from the HP synthesis section do not enter the first MP carbamate condensation section thereby providing a higher condensation temperature for heat exchange, which heat exchange may for instance be used for heating urea solution for water evaporation.

Carbamate solution from the second MP carbamate condensation section is supplied to the first MP carbamate condensation section operated at a higher temperature. Thereby water included in the carbamate solution from the LP recovery section is advantageously used for preventing carbamate crystallization in three condensers in series. For instance, in an example embodiment of the process according to the invention, carbamate solution is obtained from the LP carbamate condenser with 30 wt. % $H_2O$ and supplied to the second MP carbamate condenser (e.g. scrubber) giving carbamate solution with 26 wt. % $H_2O$, supplied in turn to the first MP carbamate condenser giving carbamate solution with advantageously a lower water content of 20 wt. % $H_2O$ that is recycled to HP synthesis.

Preferably, non-condensed gas from the first MP carbamate condensation section is supplied to the second MP carbamate condensation section. The non-condensed gas is combined with off-gas from the reactor and condensed in the second MP carbamate condensation section in preferred embodiments. Preferably, the second MP carbamate condensation section operates at lower pressure than the first MP carbamate condensation section, e.g. a pressure at least 1.0 bar lower, for instance at 1.0 to 5 bar lower.

Non-condensed gas from the second MP carbamate condensation section is for instance supplied to an absorber operated e.g. at LP. Very advantageously, inert gases from HP synthesis are not supplied to the second MP carbamate condenser in preferred embodiments thereby reducing condensable gas supply to the absorber and increasing the temperature in the heating zone for a fixed total gas pressure in the second MP carbamate condenser.

Preferably, the non-condensed gas from the first MP carbamate condensation section has a low $H_2$ content so as to avoid explosive mixtures especially in the second MP carbamate condensation section. The low $H_2$ content is achieved by upstream $H_2$ removal of MP $CO_2$ feed supplied to the first MP carbamate condensation section. Advantageously partial condensation in the first MP carbamate condensation section contributes to simple equipment, e.g. only a single condenser in said section, and heat transport to urea solution that is heated in the heating zone in heat exchanging contact with said condenser such as by turbulence at the downstream end of said condenser. For instance, the condenser is provided as a shell-and-tube heat exchanger with urea solution to be heated in the tubes and gas to be condensed in the shell side space.

Advantageously the plant preferably does not comprise an ammonia condenser and preferably does not comprise a recycle flow line for ammonia liquid.

Preferably, the plant further comprises a heating zone for heating urea solution for water and ammonia removal. Preferably, the plant comprises a liquid flow line for urea solution from a LP dissociator to said heating zone, optionally through an atmospheric flash tank. Preferably, the heating zone is in heat-exchanging contact with at least a part of said first MP carbamate condensation section; the LP dissociator is typically the LP dissociator of the LP recovery zone. Preferably, the heating zone is used for heating urea solution from an LP recovery section, in particular from an LP dissociator comprised in said LP recovery section, to contribute to water evaporation from the urea solution, in particular for preparing a urea melt. Preferably, the first MP carbamate condensation section is at least in part provided in a shell-and-tube heat exchanger, e.g. as described hereinbefore, with gas to be condensed in the shell (shell side space) and urea solution to be heated in the tubes.

The heated urea solution from the heating zone (e.g. pre-evaporator) is preferably subjected to gas/liquid separation to obtain water vapor also containing $NH_3$ and concentrated urea solution. The concentrated urea solution may have a urea content of e.g. 75 to 85 wt. %. The urea solution received at the inlet of the heating zone has for instance a urea content of 60 to 75 wt. % and comprises e.g. about 0.7 wt. % $NH_3$. Preferably, the urea concentration is increased by 5-10 wt. % (percentage point) in the heating zone. A relatively high urea concentration may be achieved by virtue of the relatively high temperature, such as 110° C., in the first MP carbamate condensation section.

The concentrated urea solution is for instance supplied to a vacuum evaporation section, optionally through a storage tank, to give a urea melt. The urea melt is for instance solidified in a finishing section such as a granulator or prilling tower. The urea melt may also be supplied e.g. to a melamine plant. Other uses are also possible.

The heating zone (pre-evaporator) is for instance operated at a pressure of less than 1.0 bar absolute, e.g. 0.3-0.8 bar absolute, such as 0.4-0.6 bar absolute.

The heated urea solution advantageously has low $NH_3$ content, for instance of less than 0.10 wt. %, such as about 0.05 wt. %. The low $NH_3$ content is desirable for storage of the solution in a urea storage tank.

The heated urea solution accordingly can be used e.g. for the production of diesel exhaust fluid (DEF) by virtue of the low $NH_3$ content, for instance by adding water to obtain the desired urea concentration of e.g. 32.5 wt. %. Water with sufficiently high purity for DEF production may be added e.g. as cleaned process condensate from a WWT section, as steam condensate, or as demineralized water. DEF is typically an aqueous urea solution of 32.5 wt. % urea and 67.5 wt. % water and preferably with an alkalinity as $NH_3$ of less than 0.2 wt. % on the basis of 32.5 wt. % urea, i.e. when the alkalinity is converted on the basis of water added or removed as necessary to have 32.5 wt. % urea. Advantageously, in the inventive process no steam stripping is necessary to achieve low $NH_3$ content.

The term 'pre-evaporator' as used herein does not imply that an evaporation section must be present in the plant. In some embodiments, the plant comprises the pre-evaporator but no evaporation section for producing urea melt.

The invention also pertains to a urea production process carried out in a urea plant of the $CO_2$ stripping type, preferably carried out in the inventive urea production plant. The urea production process comprises for instance supplying a first part of the urea synthesis solution from the reaction zone to the HP stripper and stripping the urea solution in the HP stripper using $CO_2$ as strip gas to give stripped urea solution, and supplying stripped urea solution to the MP treatment unit to give a first MP gas stream and a treated urea solution, and subjecting a second part of the urea synthesis solution from the reaction zone to carbamate decomposition by heating in the MP dissociator to give a second MP gas stream and an MP urea solution, and providing a third MP gas stream from the HP synthesis section by pressure reduction. The process involves combining and condensing two gas streams selected from the group consisting of said first, second and third MP gas stream in a first MP carbamate condensation section. Preferably, the process involves combining and condensing the first and second gas stream in said first MP carbamate condensation section and subjecting the third gas stream to condensation in a second MP carbamate condensation section.

Preferably the first MP carbamate condensation section is operated at a pressure that is higher, e.g. 1-10 bar higher, than the operating pressure of the second MP carbamate condensation section, more preferably 1-5 bar higher, even more preferably 1-3 bar higher.

Preferably, the first MP carbamate condensation section is operated at a pressure of 15-35 bar. Preferably the MP treatment unit, preferably the adiabatic flash vessel, is operated at a pressure of 15-35 bar. Preferably, the adiabatic flash vessel operated at the same pressure as the first MP carbamate condensation section. Preferably, the second MP carbamate condensation section is operated at a pressure of 15-35 bar.

Preferably, HP stripper is operated with a stripping efficiency alfa in the range 0.65-0.80, e.g. 0.70-0.75. The relatively low stripping efficiency advantageously provides for lower energy consumption by the HP stripper, e.g. lower steam consumption. Additionally, the HP stripper and HP carbamate condenser may be relatively smaller which may be advantageous for revamping existing urea plants to increase capacity with desirable limited modification of the HP synthesis section. The MP treatment unit, in particular the preferred adiabatic flash vessel, may contribute to low water recycle with the carbamate recycle even with relatively low stripping efficiency.

Preferably, 30-70 vol. % of the urea synthesis solution is supplied from the reaction zone to the MP dissociator, i.e. bypassing the HP stripper. Thereby the MP dissociator can significantly unload the HP stripper.

Also provided is the method of modifying an existing urea production plant as stated hereinabove.

Preferably, the method involves arranging the first MP carbamate condensation section to receive the first MP gas stream from the MP treatment unit and the second MP gas stream from the MP dissociator. Preferably, the method involves providing the gas flow line from the MP treatment unit to the first MP carbamate condensation section and the gas flow line from the MP dissociator to the first MP carbamate condensation section. Preferably, the method involves providing a gas flow line from the pressure reducing element to the second MP carbamate condensation section for supplying the third MP gas stream. The method generally provides for increase of the capacity of the urea plant in an advantageous way with no or few changes of the HP synthesis section.

In an interesting embodiment, the existing plant comprises the MP treatment unit, in particular an MP adiabatic flash vessel, receiving stripped urea solution and the first MP carbamate condenser. The first MP carbamate condenser receives synthesis section off-gas from the reactor and/or from the HP carbamate condenser, and gas from the MP treatment unit in the existing plant. For instance, the first MP carbamate condenser is in heat exchanging contact with a heating zone for urea solution, in particular with a pre-evaporator, in the existing plant. A preferred inventive method of modifying such an existing plant involves adding the MP dissociator which receives a part of the urea synthesis solution from the reactor to the plant, and adding the second MP carbamate condenser, and a gas flow line for supplying the third MP gas stream (e.g. reactor off-gas) to the second MP carbamate condenser and a gas flow line for supplying the gas stream from the MP dissociator to the first MP carbamate condenser. In this way advantageously the inert gases in the reactor off-gas no longer negatively affect (decrease) the temperature in the pre-evaporator. Furthermore, the various advantages as discussed in connection with the inventive plant and process are obtained in the modified plant. Very advantageously, a capacity increase of the urea plant can be obtained by the MP dissociator without adding or modifying HP equipment. The preferences described hereinabove for the urea production plant apply also for the modified urea plant, for example the liquid flow line for carbamate solution from the added second MP carbamate condenser to the first MP carbamate condenser. Preferably, the existing plant does not comprise a HP scrubber and preferably in the existing plant the synthesis section off-gas is supplied directly from the reactor and/or HP carbamate condenser to the first MP carbamate condenser through pressure reducing element such as e.g. a valve(e.g. control valve).

FIG. 1 shows an example urea production process and plant according to an embodiment of the invention. The plant comprises a high-pressure (HP) synthesis section (HPSS) which comprising an HP stripper (HPS), a reaction zone (HPR) for forming urea from $NH_3$ and $CO_2$, and a condensation zone (HPCC). The reaction zone (HPR) comprises a reactor, for instance a vertical urea reactor, with a liquid outlet for urea synthesis solution (1) and a separate gas outlet for inerts (14). A first part (1a) of the urea synthesis solution is supplied to the HP stripper (HPS) which uses $CO_2$ as strip gas. A stripped urea solution (2) from the HP stripper (HPS) is supplied to the MP treatment unit (MPTU). A second part (1b) of the urea synthesis solution is supplied to the MP dissociator (MPD) which is a heat exchanger for heating the urea solution. Thereby a single reactor is connected to supply urea synthesis solution to both the HP stripper and the MP dissociator. Gas (4) from the MP treatment unit (MPTU) and gas (5) from the MP dissociator (MPD) both comprising $NH_3$ and $CO_2$ are condensed in the first MP carbamate condensation section (MPCC-1) in heat exchanging contact with a pre-evaporation unit (PEV) used for heating a urea solution (11a) to give heated urea solution (11b). Gas (3) from the HP stripper (HPS) is condensed in the HP carbamate condenser in the condensation zone (HPCC) also receiving $NH_3$ feed to give condensate (6) that is supplied to the reactor in the reaction zone (HPR). Urea solution (7) from the MP treatment unit (MPTU) is supplied to an LP dissociator (LPD) which preferably is a shell-and-tube heat exchanger for heating the urea solution (7) so as to decompose ammonium carbamate into $NH_3$ and $CO_2$. Urea solution (8) from the MP dissociator (MPD) is also supplied to an MP stripper (MPS) where it is contacted with MP $CO_2$ feed. Urea solution (16) from the MP stripper is for example supplied to an LP recovery section, e.g. to the LP dissociator (LPD) (not shown). Gas (14) from the HP synthesis section (HPSS), e.g. gas (14) from the reactor in the reaction zone (HPR) and/or gas (14a) from the HP carbamate condenser are expanded to MP in a pressure reducing element such as e.g. one or more valve (V1) and are supplied to the second MP carbamate condensation section (MPCC-2) which also receives non-condensed gas (10) from the first MP carbamate condensation section (MPCC-1). Non-condensed gas (18) from the second MP carbamate condensation section (MPCC-2) is for instance supplied to an absorber operating at LP. Gas (12) obtained from the LP dissociator (LPD) is supplied to an LP carbamate condenser (LPCC) which also receives directly or indirectly a part of the $CO_2$ feed. The LP carbamate solution (13) having a relatively high water content from the LP carbamate condenser (LPCC) is supplied to the second MP carbamate condensation section (MPCC-2) where it helps to avoid carbamate crystallization. The MP carbamate solution (15) from the second MP carbamate condensation section (MPCC-2) is supplied to the first MP carbamate condensation section (MPCC-1) operating at higher temperature where it is advantageously enriched in carbamate. The resulting carbamate solution (9) is recycled to the HP synthesis section (HPSS), e.g. to the HP condensation zone (HPCC). The urea solution (11) obtained from the LP dissociator (LPD) optionally after further expansion steps still contains water and is e.g. heated as urea solution (11a) in the pre-evaporator (PEV) using the heat released in the first MP carbamate condensation section (MPCC-1) at advantageously high temperature, and subjected to gas/liquid separation to give water vapor and concentrated urea solution. Gas (17) from the MP $CO_2$ stripper (MPS), comprising a part of the MP $CO_2$ feed, is supplied to the first MP carbamate condensation section (MPCC-1) to contribute to an appropriate N/C ratio in said condensation section.

Preferences for the plant apply also for the process and for the revamping method (method of modifying an existing plant). The process is preferably carried out in the plant as described. The revamping method preferably gives the plant as described.

In this application, for process streams (i.e. not for steam lines), high pressure (HP) is above 100 bar, for instance 120 to 300 bar, typically 150 to 200 bar. Medium pressure (MP) is for example 10 to 70 bar (including intermediate pressure of 30 to 70 bar), in particular 10 to 40 bar, and low pressure (LP) is for example 1.0 to 10 bar, in particular 1.0 to 8 bar, e.g. 1.5 to 5 bar. All pressures are given in bar absolute.

The N/C ratio as used herein for urea solutions and carbamate streams reflects the composition of the so-called initial mixture before urea production, consisting only of $NH_3$, $CO_2$ and $H_2O$, as used in the art of urea plants, and is the molar ratio. The N/C ratio for gas streams indicates the molar ratio of $NH_3$ to $CO_2$.

The term 'carbamate' as used herein refers to ammonium carbamate, as the term is used in the art of urea plants.

The term 'typical' and 'in particular' are used to indicate features that can be used in some embodiments but that are not mandatory. Also preferred features are not mandatory.

The term 'liquid flow line' and 'liquid communication' refers to a flow line (e.g. tubing or ducts) allowing for passage of liquid between two units, optionally through a number of intermediate units. Liquid communication does not involve gas phase transport, and hence two units that are connected by an evaporator, a flow line for vapor, and a condenser are not in liquid communication, although they are in fluid communication (which encompasses both gas phase transport and liquid transport). A first unit is in liquid communication with a second unit for instance if an outlet for liquid of the first unit is connected with an inlet of a condenser and an outlet for liquid of the condenser is connected with an inlet of the second unit. A pump may for instance be present in a liquid flow line. A 'gas flow line' is a flow line for gas phase transport of gas between two units. Gas phase transport does not involve transport of the material as liquid.

The stripping efficiency (alfa) is defined as the amount of ammonia converted to urea (and biuret) divided by the total amount of ammonia, typically measured at the liquid outlet of the stripper, for a HP stripper. This definition is equivalent to that of the $NH_3$ conversion based on the outlet of the stripper. Hence, alfa=$(2*wt. \% \text{ urea}/60)/[(2*wt. \% \text{ urea}/60)+(wt. \% NH_3/17)]$, measured at the liquid outlet of the stripper, wherein wt. % $NH_3$ includes all ammonia species including ammonium carbamate. The skilled person understands that 'stripping efficiency' refers to the urea purity at the stripper liquid outlet and not to the energy efficiency of the stripper.

Condensation in a carbamate condenser refers to so-called carbamate condensation, which involves the reaction of $NH_3$ and $CO_2$ into ammonium carbamate which is a liquid, such that in effect gaseous $NH_3$ and $CO_2$ become carbamate in a liquid phase. Carbamate decomposition refers to the dissociation reaction of carbamate into $NH_3$ and $CO_2$.

As discussed hereinabove, the invention pertains to a urea production plant and a process using a high-pressure $CO_2$ stripper, downstream medium-pressure treatment unit and a medium-pressure dissociator receiving urea synthesis solution from the reactor, wherein gas from the treatment unit and dissociator are condensed in a first condenser and off-gas from the synthesis section is condensed separately in a second condenser. A revamping method is also described.

EXAMPLE

The invention will now be further illustrated by the following non-limiting example. This example does not limit the invention and does not limit the claims.

Example 1

In a process according to FIG. 1, the second MP carbamate condenser is operated at 93° C. and 21 bar and gives carbamate solution with 36 wt. % $NH_3$, 37 wt. % $CO_2$ (both free and as a carbamate for $NH_3$ and $CO_2$) and 26 wt. % $H_2O$ that was supplied to the first MP carbamate condenser. The first MP carbamate condenser was operated at 114° C. and 24 bar and yielded carbamate solution containing 38 wt. % $NH_3$, 42 wt. % $CO_2$ and 19 wt. % $H_2O$ (percentages both free and as carbamate for $NH_3$ and $CO_2$) which can be supplied to HP synthesis with the advantageous low water content.

The invention claimed is:

1. A urea production plant comprising a high pressure (HP) synthesis section comprising an HP stripper, a reaction zone for forming urea from $NH_3$ and $CO_2$, and a condensation zone, wherein the HP stripper has an inlet for $CO_2$ feed as strip gas, the plant further comprising a medium-pressure (MP) treatment unit, an MP dissociator, a first MP carbamate condensation section, and a second MP carbamate condensation section, a first flow line for urea solution from said reaction zone to said HP stripper and a second flow line for urea solution from said reaction zone to said MP dissociator, wherein the plant comprises a liquid flow line for stripped urea solution from said HP stripper to said MP treatment unit,
    wherein the MP treatment unit has a gas outlet for a first MP gas stream, wherein the MP dissociator has a gas outlet for a second MP gas stream, and wherein the HP synthesis section has a gas outlet and a pressure reducing element for a third MP gas stream,
    and wherein two gas streams selected from the group consisting of said first, second and third MP gas stream are combined and condensed in said first MP carbamate condensation section.

2. The urea production plant according to claim 1, wherein said first MP carbamate condensation section is arranged to receive said first MP gas stream from said MP treatment unit and said second MP gas stream from said MP dissociator and wherein said second MP carbamate condensation section receives said third MP gas stream.

3. The urea production plant according to claim 1, wherein said MP treatment unit is a flash vessel.

4. The urea production plant according to claim 1, further comprising:
    a liquid flow line for urea solution from said MP treatment unit to a low pressure dissociator;
    a gas flow line from said low pressure dissociator to a low pressure carbamate condenser;
    a liquid flow line for carbamate solution from said low pressure carbamate condenser to said second MP carbamate condensation section;
    a liquid flow line for carbamate solution from said second MP carbamate condensation section to said first MP carbamate condensation section;
    a liquid flow line for carbamate solution from said first MP carbamate condensation section to said high-pressure (HP) synthesis section.

5. The urea production plant according to claim 1, further comprising a heating zone for heating urea solution for water removal, wherein said heating zone is in heat-exchanging contact with at least a part of said first MP carbamate condensation section.

6. The urea production plant according to claim 1, further comprising an MP $CO_2$ stripper and a liquid flow line for urea solution from said MP dissociator to said MP $CO_2$ stripper.

7. The urea production plant according to claim 6, further comprising a gas flow line from said MP $CO_2$ stripper to said first MP carbamate condensation section.

8. The urea production plant according to claim 1, wherein the second MP condensation section comprises a shell-and-tube heat exchanger, and a downstream gas/liquid separator.

9. The urea production plant according to claim 1, wherein gas from the first MP carbamate condensation section is also supplied to the second MP condensation section;
    and wherein gas from the second MP condensation section is supplied to an absorber.

10. A urea production process carried out in a urea production plant according to claim 1, wherein the process comprises supplying a first part of the urea synthesis solution from the reaction zone to the HP stripper and stripping the urea solution in said stripper using $CO_2$ as strip gas to give stripped urea solution, and supplying stripped urea solution to the MP treatment unit to give a first MP gas stream and a treated urea solution, and subjecting a second part of the urea synthesis solution from the reaction zone to carbamate decomposition by heating in the MP dissociator to give a second MP gas stream and an MP urea solution, and providing a third MP gas stream from the HP synthesis section by pressure reduction, wherein the process involves combining and condensing two gas streams selected from the group consisting of said first, second and third MP gas stream in the first MP carbamate condensation section.

11. The urea production process of claim 10, wherein said first MP carbamate condensation section is operated at a higher pressure than said second MP carbamate condensation section.

12. The urea production process according to claim 10, wherein said first MP carbamate condensation section is operated at a pressure that is 1-10 bar higher than the operating pressure of said second MP carbamate condensation section.

13. The urea production process according to claim 10,
wherein said first MP carbamate condensation section is operated at a pressure of 15-35 bar;
wherein said MP treatment unit is operated at a pressure of 15-35 bar;
and wherein said second MP carbamate condensation section is operated at a pressure of 15-35 bar.

14. The urea production process according to claim 10, wherein the HP stripper is operated with a stripping efficiency in the range 0.65-0.80.

15. A method of modifying an existing urea production plant, the existing urea production plant comprising a high-pressure (HP) synthesis section comprising an HP stripper, a reaction zone for forming urea from $NH_3$ and $CO_2$, and a condensation zone, wherein the HP stripper has an inlet for $CO_2$ feed as strip gas and the HP synthesis section has a gas outlet, the plant comprising a first flow line for urea solution from said reaction zone to said HP stripper, the method comprising adding, if not already present in the plant, the following units and connections:
a medium-pressure (MP) treatment unit having has a gas outlet for a first MP gas stream,
an MP dissociator having a gas outlet for a second MP gas stream,
a first MP carbamate condensation section, and a second MP carbamate condensation section,
and a second flow line for urea solution from said reaction zone to said MP dissociator,
a pressure reducing element for gas from said gas outlet of said HP synthesis section giving a third MP gas stream,
a liquid flow line for stripped urea solution from said HP stripper to said MP treatment unit, the method further comprising configuring the plant such that two gas streams selected from the group consisting of said first, second and third MP gas stream are combined and condensed in a first MP carbamate condensation section and one gas stream selected from said group is condensed separately in a second MP carbamate condensation section.

16. The method of modifying an existing urea production plant according to claim 15, wherein the existing plant comprises the medium-pressure (MP) treatment unit having a gas outlet for a first MP gas stream, the first MP carbamate condensation section, and the liquid flow line for stripped urea solution from said HP stripper to said MP treatment unit, the pressure reducing element for gas from said gas outlet of said HP synthesis section giving a third MP gas stream, the method comprising providing
the MP dissociator having a gas outlet for a second MP gas stream,
the second MP carbamate condensation section, and
the second flow line for urea solution from said reaction zone to said MP dissociator, and arranging the first MP carbamate condensation section to receive said first MP gas stream from said MP treatment unit and said second MP gas stream from said MP dissociator and arranging the second MP carbamate condensation section to receive said third MP gas stream from the HP synthesis section.

17. The urea production plant according to claim 2, wherein said second MP carbamate condensation section comprises a condenser, scrubber and/or absorber.

18. The urea production process of claim 10, wherein the process involves combining and condensing the first and second gas stream in the said first MP carbamate condensation section and subjecting the third gas stream to condensation in a second MP carbamate condensation section.

19. The urea production process of claim 10, wherein said MP treatment unit is an adiabatic flash vessel operated at the same pressure or higher pressure as the first MP carbamate condensation section.

20. The method of modifying an existing urea production plant according to claim 15, further comprising arranging the first MP carbamate condensation section to receive said first MP gas stream from said MP treatment unit and said second MP gas stream from said MP dissociator and arranging the second MP carbamate condensation section to receive said third MP gas stream.

* * * * *